United States Patent
Chynoweth et al.

(10) Patent No.: US 7,153,428 B2
(45) Date of Patent: Dec. 26, 2006

(54) FLOODED DENSIFIED LEACHBED ANAEROBIC DIGESTION

(75) Inventors: David P. Chynoweth, Gainesville, FL (US); Arthur A. Teixeira, Gainesville, FL (US); John M. Owens, High Springs, FL (US); Patrick J. Haley, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 76 days.

(21) Appl. No.: 11/117,269

(22) Filed: Apr. 28, 2005

(65) Prior Publication Data

US 2006/0060524 A1    Mar. 23, 2006

Related U.S. Application Data

(60) Provisional application No. 60/566,515, filed on Apr. 28, 2004.

(51) Int. Cl.
*C02F 3/28* (2006.01)
*C02F 11/04* (2006.01)
*C05F 17/02* (2006.01)

(52) U.S. Cl. .................. 210/603; 210/613; 210/97; 210/173; 210/175; 210/259; 210/903; 71/10

(58) Field of Classification Search .......... 210/603, 210/605, 612–613, 97, 173, 175, 252, 259, 210/903; 71/10, 21, 23, 25
See application file for complete search history.

(56) References Cited

U.S. PATENT DOCUMENTS 3,700,590 A * 10/1972 Burton .................. 210/615
4,336,135 A    6/1982 Price
4,735,724 A *  4/1988 Chynoweth et al. ........ 210/603
5,269,634 A   12/1993 Chynoweth et al.
5,525,230 A *  6/1996 Wrigley et al. ............. 210/618
2003/0175942 A1 9/2003 Kim et al.

FOREIGN PATENT DOCUMENTS

JP         61-120698      *  6/1986

OTHER PUBLICATIONS

Chynoweth, D. et al. (Jul. 15, 2002) "Anaerobic Digestion For Reduction and Stabilization of Organic Solid Wastes During Space Missions: Laboratory Studies" 32 Internat. Conf. Environ. Systems, Paper 2002-01-2351, XP002353193.

* cited by examiner

*Primary Examiner*—Fred G. Prince
(74) *Attorney, Agent, or Firm*—Saliwanchik, Lloyd & Saliwanchik

(57) ABSTRACT

The present invention provides improved systems and processes for performing sequential batch anaerobic composting (SEBAC) on high solids content wastes. In particular, the present invention provides improved flooded SEBAC systems that function more efficiently (i.e., higher conversion kinetics) at lower temperatures than conventional SEBAC systems. Further, the improved flooded SEBAC systems and processes of the subject invention enable efficient anaerobic digestion operation at a smaller reactor volume ratio as compared to conventional SEBAC systems, without the displacement of leachate and clogging as a result of entrapped biogas or an increased pressure drop (hydraulic). Further, the improved flooded SEBAC systems of the invention overcome concerns associated with leachate displacement as well as excessive pressure drops.

21 Claims, 4 Drawing Sheets

FLOODED DENSIFIED LEACHBED ANAEROBIC DIGESTION

CROSS-REFERENCE TO A RELATED APPLICATION

This application claims the benefit of U.S. provisional application Ser. No. 60/566,515, filed on Apr. 28, 2004, which is hereby incorporated by reference in its entirety, including any figures, tables, or drawings.

GOVERNMENT SUPPORT

The subject invention was made with government support under a research project supported by the National Aeronautics and Space Administration under grant number NCC 9-110. The government has certain rights to the invention.

BACKGROUND OF INVENTION

Many approaches for waste disposal are currently available. For example, sanitary landfills formed by filling a land area with successive layers of solid waste and layers of earth or soil are well known. Unfortunately, such landfills have the potential for producing large amounts of a hazardous, explosive gas (methane), which may migrate to buildings or structures several hundred feet from the landfill if not removed from the landfill. Further, the natural precipitation draining out of the landfill may carry toxic, polluted water to contaminate underground water supplies, surface streams, and wells. Due to the very slow stabilization of waste, a landfill may not be used for other purposes for long periods of time and, thus, particularly near metropolitan areas, represents a large waste of land.

Other approaches utilize anaerobic digestion for stabilization and conversion of organic wastes to methane and compost. In general, such anaerobic designs convert a large fraction of organic matter (>50%) to methane and carbon dioxide without the need for hydrolysis as a pretreatment step or extensive external energy requirements to remove water (i.e., with thermal processes) or pretreatment and product recovery (i.e., with bioethanol).

One such anaerobic design utilizes a leachbed anaerobic composting process (hereinafter the SEBAC system or process) for the anaerobic digestion of high-solids organic feedstocks, as disclosed in U.S. Pat. No. 5,269,634. In this process, coarsely shredded feedstock is placed into a bioreactor and leachate from a mature bioreactor recycled between the mature bioreactor and the newly loaded bioreactor to provide moisture, inoculum, nutrients, and buffer necessary to start up the newly loaded bioreactor. Such bioreactors, however, require a great deal of volume due to the bulk density of organic solids introduced into the bioreactors. Further, for efficient composting, such bioreactors must be maintained at thermophilic levels (about 55° C.); which require a great deal of expensive energy input.

To address these deficiencies, improved SEBAC systems have been proposed (see Chynoweth, D. et al., "Anaerobic Digestion for Reduction and Stabilization of Organic Solid Wastes During Space Missions: Laboratory Studies," 32 *Internat. Conf. Environ. Systems (ICES)*, paper 2002-01–2351 (Jul. 15, 2002)) in which SEBAC bioreactors are flooded and leachate is forcibly pumped between the flooded bioreactors. Unfortunately, within the bioreactors of such flooded SEBAC systems, generated biogas often becomes entrapped in the densified solid waste and displaces a significant volume of leachate into the biogas line. This causes a loss of liquids within the enclosed system, which is a concern because it affects proper function of SEBAC systems.

Further, during flooded SEBAC operation when introducing newly filled bioreactor(s), the flow of leachate through the leachbed of mature bioreactor(s) is impeded or may even cease, in spite of the use of positive displacement pumps. Specifically, when floatation of waste residue comes into contact against an upper screen of a newly filled bioreactor, an increase in pressure drop (hydraulic pressure) across the reactor bed is observed. Without the flow of leachate through the flooded SEBAC system, liquid flow through the reactor may cease and thus hinder anaerobic digestion of organic solid wastes.

Accordingly, an improved flooded SEBAC system and process for the efficient anaerobic conversion of organic wastes is needed to address the deficiencies noted above, namely displaced leachate as a result of biogas entrapment and impeded leachate flow, both of which result in increased hydraulic (leachate) pressure in bioreactors and hindrance of anaerobic digestion of organic wastes.

BRIEF SUMMARY OF THE INVENTION

The present invention provides an improved flooded SEBAC system in which bioreactor sizes are reduced and efficient waste processing occurs at lower temperatures than those previously required for conventional SEBAC systems. The systems and processes of the present invention include flooded SEBAC systems in which bioreactors operate in flooded conditions (i.e., no headspace in a bioreactor), at least one external vessel to which only leachate siphoned from the top or bottom portion or area between the top and bottom portion (i.e., center) of a bioreactor is placed, means for continuously sensing hydraulic pressure in a bioreactor; and means for leachbed flow reversal upon detection, by the sensing means, of an increase in pressure drop (hydraulic) as compared to an established threshold.

In accordance with the subject invention, SEBAC systems and processes disclosed in U.S. Pat. No. 5,269,634; and flooded SEBAC systems and processes described by Chynoweth, D. et al., "Anaerobic Digestion for Reduction and Stabilization of Organic Solid Wastes During Space Missions: Laboratory Studies," 32 *Internat. Conf. Environ. Systems (ICES)*, paper 2002-01–2351 (Jul. 15, 2002) and Xu, Q. et al., "Anaerobic Digestion for Reduction and Stabilization of Organic Solid Waste During Space Missions: Systems Analysis," 32 *Internat. Conf. Environ. Systems (ICES)*, paper 2002-01–2351 (Jul. 15, 2002) are incorporated herein by reference in their entirety.

High-solids leachbed anaerobic digestion (HSLAD) provided by the subject invention involves a solid-phase fermentation with leachate recycle between new reactors (where leachate has not yet been introduced to the waste stored therein) and old reactors (where leachate has already been introduced to the waste stored therein) for inoculation, wetting, and removal of volatile organic acids during startup. After anaerobic conversion is complete, the compost bed can be treated for future use. For example, the compost is treated for use in biofiltration and plant growth medium. The nutrient-rich leachate can be used for additional HSLAD systems and/or processes of the invention or used as a vehicle for nutrient recycle.

In one embodiment, improved HSLAD systems and processes of the subject invention include flooded SEBAC systems and processes having at least one bioreactor that is flooded; a means for forcing leachate through feedstock beds; a means for separating biogas from leachate in a gas collection reservoir; a means for accumulating and storing displaced leachate, wherein leachate is collected from any portion of bioreactor(s), including the top, central, and/or bottom portion; means for continuously sensing hydraulic pressure in a bioreactor; and means for reversing leachbed flow upon detection by the sensing means of an increase in pressure drop (hydraulic) across the system, as compared to an established pressure threshold.

In another embodiment, the HSLAD system of the invention includes SEBAC systems in which bioreactors are flooded; at least one external vessel to allow for accumulation and storage of leachate alone, wherein the leachate is collected from the central portion of a bioreactor; means for continuously sensing hydraulic pressure in a bioreactor; means for leachbed flow reversal upon detection by the sensing means of an increase in pressure drop (hydraulic) as compared to an established threshold; and pumping means for passing leachate through the high density bioreactor beds (flooded) with limited hydraulic conductivity. According to the present invention, the flooded design of the bioreactor(s) permits leachate recycle through leachbeds without dependence upon gravity, as previously required for conventional SEBAC systems.

In a further embodiment, an HSLAD system of the invention includes SEBAC systems in which bioreactors are flooded; at least one external vessel to allow for accumulation and storage of leachate collected from the central portion of a bioreactor; means for continuously sensing hydraulic pressure in a bioreactor; means for leachbed flow reversal upon detection by the sensing means of an increase in pressure drop (hydraulic) as compared to an established threshold; and an external vessel for gas-liquid separation. In a related embodiment, when operating the HSLAD system of the invention under non-terrestrial conditions, the gas would separate from the leachate by gravity in the external vessel. Alternatively, under terrestrial or microgravity conditions, a gas-liquid separation process (e.g., centrifugal) could be employed on the contents of the external vessel.

In certain embodiments, the improved HSLAD systems and processes of the invention can be applied to organic high solid wastes, including solid waste (e.g., paper, cardboard, wood, leaves), landfill waste streams, waste produced from the processing of products from manufacturing facilities such as meat/poultry packing, beer and wine making, and other food industries (sugar beets, potatoes, corn, dog food, etc.), water treatment waste/sludge; waste generated by the recycling industry, coal, peat, agricultural wastes (waste generated by feedlot operations; e.g., poultry and cow manure mixed with bedding materials such as straw), biosolids (i.e., yard wastes including woods and grasses), human wastes (dry or wet), inedible plant residues, trash, packaging materials, (e.g., paper, tape), filters, and other miscellaneous wastes (Verostko, C. et al., "Solids Waste Processing and Resource Recovery for Long-Duration Missions—A workshop," *ICES Conference, Orlando, Fla.*, Paper 01–2351 (2001)). In one embodiment, the organic solid wastes that are loaded into an improved HSLAD system and process of the invention include, but are not limited, to several food crop residues such as wheat, potato, sweat potato, tomato, peanut, and rice.

An advantage of the invention is the improved performance in generating biogas and compost as compared to conventional and previously disclosed flooded SEBAC systems.

DETAILED DISCLOSURE

Figure 1:
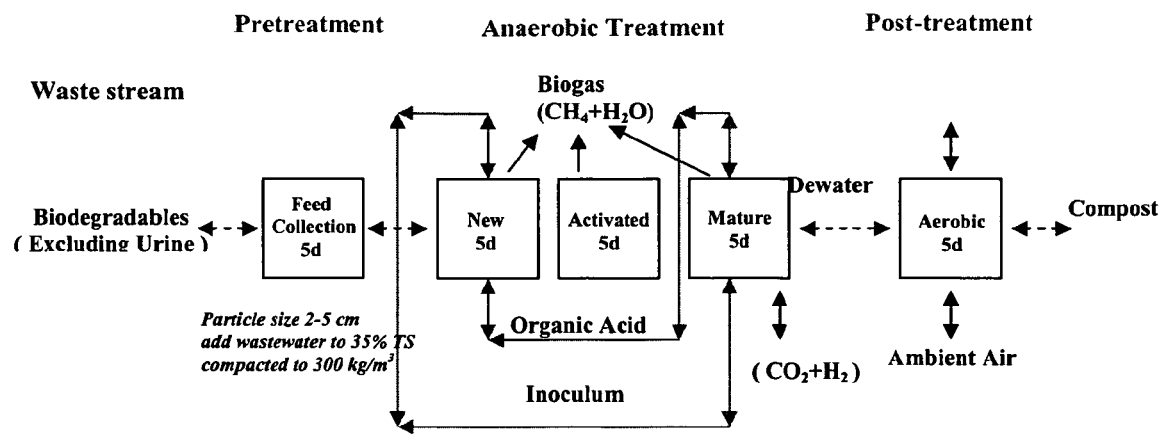
FIG. 1 is a flow diagram illustrating the steps of an improved HSLAD process of the subject invention.

The present invention provides improved systems and processes for performing sequential batch anaerobic composting (SEBAC) on high solids content wastes. In particular, the present invention provides improved flooded SEBAC systems that function more efficiently (i.e., higher conversion kinetics) at lower temperatures than conventional SEBAC systems. Further, as illustrated in the following Table 1, the improved flooded HSLAD systems and processes of the subject invention enable efficient anaerobic digestion operation at a smaller reactor volume ratio as compared to conventional and/or previously disclosed flooded SEBAC systems, without the displacement of leachate and clogging as a result of entrapped biogas or increase in pressure drop (hydraulic), respectively. Further, the improved flooded HSLAD systems of the invention overcomes concerns with leachate displacement and excessive hydraulic pressure drops normally observed in flooded SEBAC systems.

In accordance with the subject invention, improved HSLAD systems and processes convert organic matter having a high solids content into useful microbial fermentation products and compost. Organic high solids wastes of the invention include bulk waste that cannot be transported or handled as a liquid.

The present invention provides improved HSLAD systems and processes that reduce volume and weight of inorganic nutrients; stabilize and recover inorganic nutrients; stabilize compost; and recover carbon dioxide and methane from biodegradable waste fractions while maintaining efficient anaerobic digestion operations.

In another embodiment, improved HSLAD systems and processes of the invention are applicable to non-terrestrial applications. For example, HSLAD systems and processes of the subject invention are used to process solid wastes generated during space missions, including reducing and stabilizing the organic fraction of solid wastes generated in space. HSLAD systems and processes have the advantage over previously known SEBAC systems in that the subject invention enables effective production of methane, carbon dioxide, nutrients, and compost as valuable, recyclable products without the need for oxygen or high temperature and pressure in both terrestrial and non-terrestrial applications.

In another embodiment, an HSLAD system of the subject invention comprises (1) at least three bioreactors including one bioreactor for feed collection and compaction; at least one bioreactor for anaerobic composting, and at least one bioreactor for post-treatment processing, wherein, during operation, the bioreactors are all flooded with no headspace; (2) an external gas/liquid separator; (3) means for accumulating and storing displaced leachate collected from the top, central, and/or bottom portion of a bioreactor; (4) means for continuously sensing hydraulic pressure in the HSLAD system; and (5) means for reversing leachbed flow upon detection by the sensing means of an increase in pressure drop (hydraulic) as compared to an established threshold. In a preferred embodiment, an HSLAD system comprises five bioreactors, wherein one bioreactor is utilized for feed collection and compaction; three bioreactors are utilized for anaerobic composting; and one bioreactor is used for post-treatment processing.

In a method of use, organic solid wastes are collected, coarsely shredded, mixed with a liquid (i.e., wastewater) to provide a pre-established moisture content, and compacted. The compacted solid waste is then loaded into an anaerobic bioreactor of the subject invention and a liquid (such as de-chlorinated water) is added until no headspace is observed in the bioreactor. Any biogas that is generated by anaerobic digestion is treated to recover carbon dioxide and remove hydrogen sulfide and other contaminants. The biogas (for example, methane) could then be used for energy (such as in a fuel cell) or discarded. The final compost resulting after anaerobic digestion can then be dewatered, treated with air to oxidize reduced residues, and heated to insure inactivation of pathogens. After this process, the final compost product and associated nutrient-rich material (i.e., water) can be applied toward agricultural use as solid substrate and as a source of nutrients for plant growth.

In a preferred embodiment, organic solid wastes are collected, coarsely shredded, mixed with wastewater to yield solid waste at less than about 35% solids; and compacted to a density of 300 $kg_{dw}/m^3$. According to the subject invention, this collection/pre-treatment step for organic solid wastes can be performed within 30 days; preferably within 14 days, more preferably within 5 days of treatment. Further, the collection/pre-treatment step can be conducted in a single reactor. The compacted solid waste is then loaded into an anaerobic bioreactor of the subject invention and de-chlorinated water is added until no headspace is observed in the bioreactor.

Biogas generated by the process is collected, treated, and then can be used for energy (i.e., in a fuel cell) or discarded (i.e., flared). The final compost resulting after anaerobic digestion is dewatered and treated with air to oxidize reduced residues for a period of about 1 week, preferably for a period of 1–5 days, more preferably for a period of 1–2 days. The final compost after treatment with air is then heated for at least ½ hour, preferably 1 hour, at temperatures that can inactivate pathogens. In a preferred embodiment, final, post air treated compost is heated at about 50–80° C., preferably at 70° C. or higher for at least one hour, to insure inactivation of pathogens. In certain embodiments, the final, post air treated compost is subject to irradiation or chemicals compounds known to be toxic to pathogens (such as ethylene oxide gas).

The subject invention provides HSLAD systems and processes that reduce the volume of high solids waste (also referred to herein as "feedstock(s)") on a dry weight basis by about 2–4 fold or more via saturation with a liquid followed by compaction. As contemplated herein, the liquid used for saturation can include water such as recycled water, wastewater, as well as fresh water. With reduced volume of feedstock, the reactor size (volume) and mass for HSLAD systems and processes of the invention are significantly reduced. In a preferred embodiment, the reactor system size can be reduced from the conventional SEBAC reactor volume of 3.2 $m^3$ (see Verostko, C. et al., "Solids Waste Processing and Resource Recovery for Long-Duration Missions—A workshop," *ICES Conference, Orlando, Fla.,* Paper 01–2351 (2001)) to a reactor having a volume of about 1 $m^3$. Compaction of feedstock to higher densities (about 300 $gk/m^3$), in accordance with the subject invention, is a major parameter influencing the size of this system and giving it an advantage over aerobic composting as well as conventional SEBAC systems and methods.

In one embodiment, biochemical methane potential assays (also referred to herein as "BMP") are conducted on the biogas produced by HSLAD systems and processes of the subject invention as an indication of biodegration rates for organic solid waste. Rates of biodegradation determined by such assays are useful in that such rates influence the conversion kinetics of feedstock blends and bioreactor volume and weight requirements. According to the subject invention, BMPs provide a simple and valuable method for comparing and screening several different feedstocks for methane yield and conversion efficiency and kinetics under known conditions for aerobic digestion. Actual performance in a digester is dependent upon design and operating conditions such as residence time and temperature.

As understood by the skilled artisan, for every 10° C. increase in temperature, a doubling of kinetics is expected. As summarized in Table 1, the improved flooded HSLAD operation of the invention resulted in about a 2× improvement in conversion kinetics as compared with a conventional SEBAC system. Advantageously, improved conversion kinetics occurred in HSLAD systems/processes of the invention in spite of the 20° C. difference in operating temperature. The improvements of flooding and feedbed densification are related in that flooded operation allows the use of forced pumping (instead of reliance on gravity) to move leachate through the leachbeds. Further, by including additional improvements such as leachate surge reservoir(s) and means for reverse leachate flow to ensure proper HSLAD operation, the effect is an estimated 6×increase in capacity/unit reactor volume, which translates into a 1/6 reduction in reactor size.

TABLE 1

Differences in conventional SEBAC and improved HSLAD bioreactor design and operation and expected effect on capacity

| Parameter | Normal SEBAC | Improved HSLAD | Effect on capacity |
|---|---|---|---|
| Flooded no-headspace; external gas/liquid separator | N/A | Yes | 2× |
| Feedbed density, $kg/m^3$ | 100 | 300 | 3× |
| Operation Temp | 55° C. | 35° C. | Expected −2×, observed +2× |

In certain embodiments, at least one leachate surge reservoir is provided that is external to the bioreactors. The size of an external vessel for storing surge leachate, as compared to a bioreactor volume, is at least 1/6 the volume/size of a bioreactor. In certain embodiments, a leachate surge reservoir is 1/5, 1/4, 1/3, 1/2, 1/1 the size of a bioreactor volume/size.

In one embodiment of the invention, a flooded SEBAC system is provided in which the flow of leachate through a leachbed (densified solid waste in a bioreactor) is reversible. During flooded operation, leachate is pumped from a reservoir located in the bottom of at least one reactor. A mature reactor shares a leachate reservoir with a newly filled reactor. A portion of biogas is created under the residual solid waste material in the mature leachbed and floats the densified solid waste material within the reactor against the upper screen. At some point, the pressure drop impedes flow of leachate through the leachbed. In certain circumstances, the flow of leachate through the leachbed may cease, in spite of the use of positive displacement pumps. The present invention addresses this problem by providing a means for continuous sensing of hydraulic pressure and means for flow reversal of leachate through the leachbed when the sensing means detects an increase in pressure drop (hydraulic) as compared against an established threshold. Thus, according to the present invention, periodic reversal of leachate flow (as a result of pressure drops) enables proper, continuous flow of leachate through the HSLAD system of the invention to allow operation at design flow rates.

In a preferred embodiment, means for reversing leachbed flow include positive displacement pumps. Positive displacement pumps contemplated for use with the subject improved HSLAD system include, without limitation, bellows, double-diaphragm, flexible impeller, gear, oscillating, piston, progressing cavity, rotary lobe, rotary vane, and peristaltic pumps.

According to the present invention, an established threshold for leachate (hydraulic) pressure is dependent upon the design and operating conditions of an improved HSLAD system of the invention. Hydraulic pressure sensors can be used in accordance with the subject invention to monitor hydraulic pressure of fluid flow in any one or all of the bioreactors. Examples of hydraulic pressure sensors used in the subject invention include, but are not limited to, capacitive sensors, piezoresistive sensors, and optical sensors.

As described above, a flooded SEBAC system can periodically have significant volumes of leachate displaced as a result of entrapment of intermittent biogas in the densified solid waste in the reactor(s). Accordingly, in one embodiment, at least one leachate reservoir (also referred to herein as the surge volume) is provided wherein the reservoir is connected to the top, bottom, and/or any area between the top and bottom of a reactor of a flooded SEBAC system. The surge volume of the invention enables the accumulation and storage of displaced leachate as a result of entrapped biogas with the improved HSLAD system. Specifically, displaced leachate can diffuse through the waste to allow the leachbed to accept this volume of leachate to return.

In certain embodiments, the leachate reservoir can be heated to temperatures of 35° C. or higher to ensure optimal conditions for leachate storage. According to the subject invention, any commercially available method for heating a liquid or a vessel (containing a liquid) may be used to heat the leachate reservoir including, for example, electrical energy, steam energy, gas energy, etc., with or without heat exchangers known to the skilled artisan to be useful in heating liquids. In a related embodiment, biogas generated by the HSLAD system of the invention is utilized as a means for heating a leachate reservoir.

The leachate reservoir of the subject invention can be of any size suitable for effective performance of an HSLAD system of the invention including, but not limited to, 1/6, 1/5, 1/4, 1/3, 1/2 and 1/1 the size of a bioreactor. The from a leachate reservoir (or vice versa) can be monitored using commercially available sensing means, including, thermocouplers (which can also be used to heat leachate reservoirs) that can detect liquid flow at the outlets from the leachate reservoir.

In a method of use, as illustrated in FIG. 1, organic high solid wastes are collected, then pretreated (i.e., shredding and compaction). Once the organic waste (or feedstock) has been properly pretreated in accordance with the subject invention, leachate from a mature bioreactor is added. Leachate is recirculated between bioreactors, including the removal of leachate displaced by intermittent biogas presence in leachbed. As anaerobic digestion proceeds in accordance with the invention, biogas is collected for future use. Once anaerobic digestion of feedstock is complete, the feedstock is dewatered (leachate removal) and air is introduced for aerobic digestion to produce final compost.

The leachate of the invention preferably comprises activated cultures of microorganisms capable of digesting organic wastes. In certain embodiments, the leachate contains activated cultures of hydrolytic and methanogenic anaerobic microorganisms. The leachate of the invention is used for many purposes including, but not limited to, inoculating new reactors; transferring active microorganisms to provide nutrients, and removing volatile organic acids and gaseous by-products.

Feedstock Selection and Analysis

The improved HSLAD systems and processes of the invention can be applied to a variety of organic high solid wastes including, but not limited to, solid waste (e.g., paper, cardboard, wood, leaves), landfill waste streams, waste produced from the processing of products from manufacturing facilities such as meat/poultry packing, beer and wine making, and other food industries (sugar beets, potatoes, corn, dog food, etc.), water treatment waste/sludge; waste generated by the recycling industry, coal, peat, agricultural wastes (waste generated by feedlot operations; e.g., poultry and cow manure mixed with bedding materials such as straw), biosolids (i.e., yard wastes including woods and grasses), human wastes (dry or wet), inedible plant residues, trash, packaging materials, (e.g., paper, tape), filters, and other miscellaneous wastes (Verostko, C. et al., "Solids Waste Processing and Resource Recovery for Long-Duration Missions—A workshop," *ICES Conference, Orlando, Fla.*, Paper 01–2351 (2001)). In one embodiment, the organic high solid wastes that are loaded into an improved HSLAD system and process of the invention include, but are not limited, to several food crop residues such as wheat, potato, sweat potato, tomato, peanut, and rice.

Further, the improved HSLAD systems and processes of the invention can be applied to a variety of industries including, but not limited to, meat packing plants; sausages and other prepared meats; poultry slaughtering and processing; creamery butter; cheese; natural and processed; dry, condensed and evaporated dairy products; ice cream and frozen deserts; fluid milk; canned specialties; canned fruits and specialties; dried and dehydrated fruits, vegetables and soup mixes; pickles, sauces, and salad dressings; frozen fruits and vegetables; frozen specialties; flour and other grain mill products; cereal breakfast foods; rice milling; wet corn milling; dog and cat food; prepared feeds; raw cane sugar; cane sugar refining; beet sugar; cottonseed oil mills; soybean oil mills; vegetable oil mills; animal and marine fats and oils; edible fats and oils; malt beverages; malt; wines, brandy, and brandy spirits; distilled and blended liquors; potato chips and similar snacks; logging; sawmills and planing mills, general; hardwood dimension and flooring mills; special product sawmills; millwork; wood kitchen cabinets; hardwood veneer and plywood; softwood veneer and plywood; structural wood members; wood household furniture; upholstered household furniture; wood television and radio cabinets; wood office furniture; wood partitions and fixtures; pulp mills; paper mills; and paperboard mills.

According to the subject invention, feedstocks can be selected based on biochemical methane potential (BMP) assays. A BMP assay to determine the ultimate biodegradability (and associated methane yield) and conversion kinetics during the anaerobic methanogenic fermentation of organic substrates can be performed using methods as described by Owen et al., "Bioassay for Monitoring Biochemical Methane Potential and Anaerobic Toxicity," *Wat. Res.*, 13:485–492 (1979). These methods involve batch incubation of a substrate under conditions ideal for anaerobic decomposition (i.e., broad spectrum inoculum, excess inoculum, excess nutrients, substrate concentration below inhibitory levels, excess buffering capacity, moderate temperature, and strict anaerobic conditions).

In one embodiment, a 10-L inoculum (for BMP assays) semicontinuously-fed stirred, flooded SEBAC bioreactor was operated with dog food (Science Diet Large Canine Growth Formula, Hill Pet Nutrition, Inc.) as a feedstock. The flooded SEBAC digester was operated at a loading rate of 1.6 g VS per L per day, and hydraulic retention time of 20 days. At steady state, it exhibited a methane gas content of 57%, methane yield of 0.33 L per g VS added, and methane production rate of 0.53 $LCH_4/Lreactor/d$.

The conditions for BMP assays for the embodiment described above included 100 mL culture volume in 250-mL serum bottles, inoculum from the inoculum digester (described above), an inoculum-to-feedstock ratio of 2:1 (volatile solids basis), feedstock concentration of 2 g/L (VS basis), and incubation temperature of 35° C. Total gas and methane production were measured (i.e., several times per week) during the initial stages of the assay as well as for the final stages. Both gas production (i.e., using a graduated syringe) and methane content (i.e., by thermal conductivity gas chromatography) were measured. Samples were run in triplicate and controls included inoculum and inoculum plus Avicel cellulose. These batch serum bottle reactors were incubated until no further gas production could be detected (typically 30 days).

In a preferred embodiment, feedstock comprises either wheat or and a bled of rice residue, paper, and dog food. The feedstock was then introduced to an HSLAD system of the invention that includes SEBAC systems in which five bioreactors are flooded; two external vessels to allow for accumulation and storage of leachate collected from the portion between the top and bottom (i.e., central portion) of the bioreactors; positive displacement pumps for sensing an increase in pressure drop (hydraulic) in the bioreactors; a first pump for performing leachbed flow reversal; an external vessel for gas-liquid separation; and a second pump for passing leachate through the high density bioreactor beds (flooded) with limited hydraulic conductivity. Conversion efficiencies of 75% (for wheat-based feedstock) and 85% (for blend of rice residue, paper, and dog food feedstock) are obtained at residence times ranging from 15–25 days. In a related embodiment, the leachate recycle rates are increased to reduce volatile organic acids (VOA) accumulation and improve process kinetics.

Digester System

Conventional SEBAC designs (see U.S. Pat. No. 5,269,634) depend on gravity for leachate recycle and gas collection. Disclosed flooded SEBAC designs remove the requirement for gravity in leachate recycle and gas collection by modifying conventional SEBAC systems to include no-headspace/flooded operation and gas separation in an external vessel. Flooded operation permits forced pumping of leachate between reactors without dependence upon gravity.

Such flooded designs are flawed. Previously disclosed flooded designs do not account for intermittent biogas entrapment in the densified high solid waste in the reactors (rather than escape into biogas outlets), which thereby displaces significant volumes of leachate. Displaced leachate can result in a variety of difficulties in efficient HSLAD operation. For example, due to increased pressure from both entrapped biogas and leachate, there is a greater likelihood of (a) physical damage to bioreactor; (b) leachate contamination of collected biogas; and (c) interruption of anaerobic digestion in bioreactor.

Moreover, with previously disclosed flooded operations, drops in hydraulic pressure occur frequently, which impede the flow of leachate through the leachbed in a bioreactor. To address this problem, positive displacement pumps were used in attempts to agitate the leachbed and ensure proper leachate flow. Unfortunately, only sub-optimal leachate flow was provided using this solution.

Accordingly, the present invention provides improved HSLAD systems and processes including (1) at least three bioreactors including one bioreactor for feedstock shredding and compaction; at least one bioreactor for anaerobic composting, and at least one bioreactor for post-treatment processing, wherein the bioreactors are all flooded with no headspace; (2) an external gas/liquid separator; (3) means for accumulating and storing displaced leachate collected from the top, central, and/or bottom portion of a bioreactor, depending on the flow of the leachbed; (4) means for continuously sensing hydraulic pressure in a bioreactor; and (5) means for reversing leachbed flow upon detection by the sensing means of an increase in pressure drop (hydraulic) as compared to an established threshold.

EXAMPLE 1

Improved HSLAD Digester/Bioreactor

Figure 2:
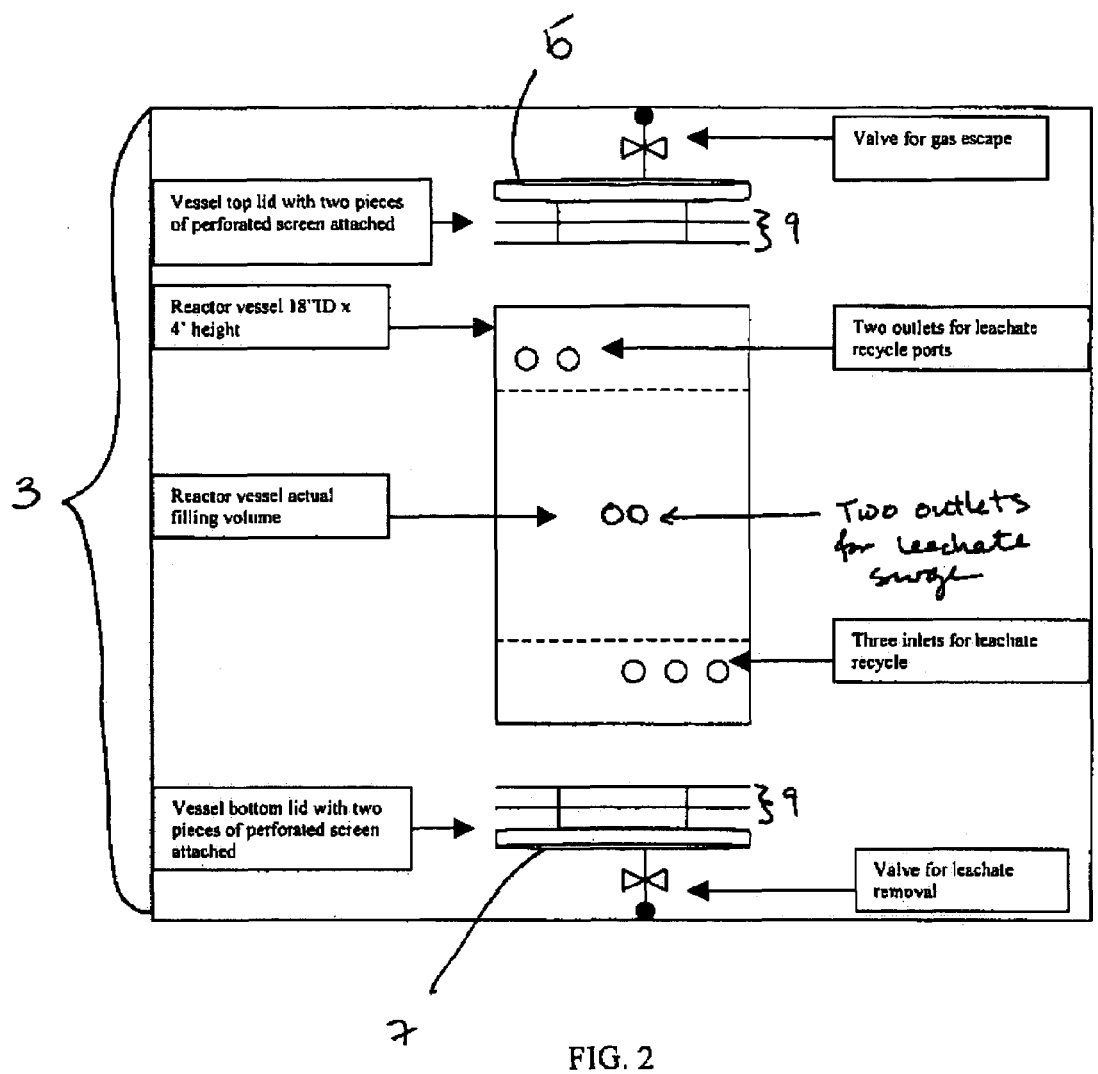
FIG. 2 is a schematic diagram of a bioreactor of the subject invention.
Figure 4:
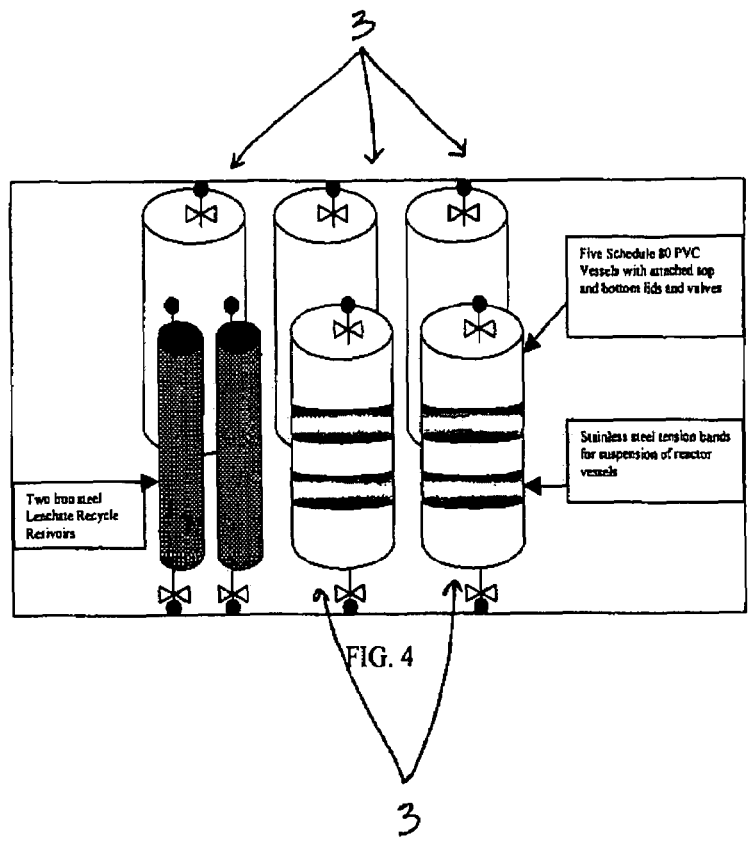
FIG. 4 is schematic diagram of a complete improved HSLAD system of the subject invention.
Figure 3:
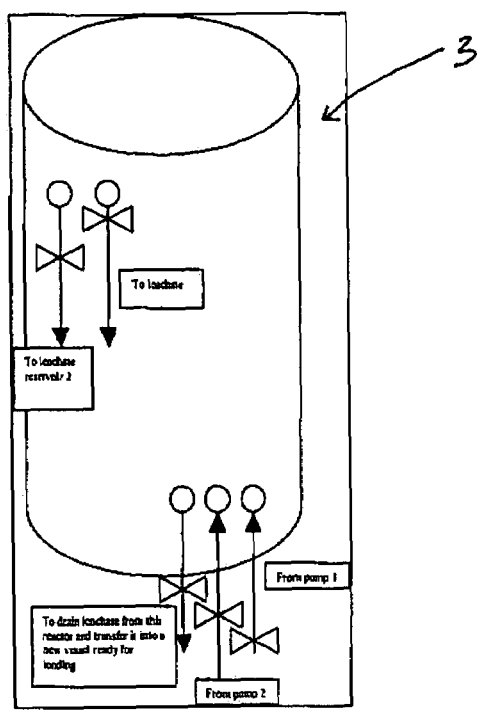
FIG. 3 is a schematic diagram of leachate flow portals in a bioreactor of the subject invention.

In one embodiment, as illustrated in FIGS. 2–4, an improved HSLAD of the invention is comprised of at least one bioreactor 3. Preferably, five cylindrical loading vessels comprise an improved HSLAD of the invention. Each vessel is constructed of schedule 80 PVC with a 17.5" ID (20"OD) and is 47.5" in height; the total volume of the cylinder is 6.6 $ft^3$ (0.19 $m^3$). Each bioreactor cylinder 3 is fitted with a top 5 and bottom 7 lid. The lids 5,7 are constructed of 20" OD, 1" thick PVC. In certain embodiments, lids include screening means 9. Preferably, lids 5,7 have two pieces of 17.5"OD perforated steel screens (⅛" holes) suspended at a distance of 3.25" and 5.5" from four steel bolts in the lid itself. The screens 9 function as a barrier to prevent biomass particles from clogging the leachate recycle lines. The total working volume of the vessel is thus reduced to 4.9 $ft^3$ (0.14 $m^3$), from a 1' loss in height due to the screens. The lids 9 are attached to the body of the vessel 3 using known attachment means such as DE-STA-CO #331 quick release clamps. Each lid 5,7 is equipped with 10 evenly spaced clamps around the perimeter of the vessel. Both the top 5 and the bottom 7 lids are tapped and a ½" PVC valve is attached for drainage of leachate or escape of gas.

Five bioreactors 3 are suspended from the ground via two stainless steel tension bands attached to a steel frame platform. Two additional iron steel 8" ID×48" cylinders are mounted to the steel frame of the system and function as the leachate recycle and surge volume vessels. The leachate recycle vessels are sealed at the bottom and fitted with an electric water heater with a built-in thermostat (Tempco TSPO2081) for heating the leachate. The leachate recycle vessels have a ¾" PVC removable top with a ⅜" brass fitting to allow gas to escape and be counted at the gas collection device (wet tip gas meter). Lids are attached to the leachate recycle vessels using four DE-STA-CO #331 quick release clamps.

Each bioreactor is tapped with at least one port, which can be located on the bottom, center, and top of the bioreactors to allow for the flow of leachate through the bioreactor and for the escape and return of leachate from the bioreactor during either reversed or unreversed leachbed flow operation. In one embodiment, bioreactors are tapped with at least one, preferably three, ½" iron ports with a 90° elbow on the bottom side (2" from the bottom), at least one, preferably two, ½" iron ports with a 90° elbow on the central area of the bioreactor (20"–25" from the top or bottom), and at least one, preferably two, ½" iron ports with a 90° elbow on the top side (2" from the top).

In a related embodiment, at least one port on the bottom of the bioreactor allows for the upflow movement of leachate through the bed of the reactor and out at least one port located on the top of the reactor system. The bottom port(s) that allow flow into the reactor are each connected to a pumping line. These pumping lines allow for the flow of leachate to go into any combination of the bioreactors. In a preferred embodiment, the bottom port(s) pumping lines are directly attached to a Monyo ½" inlet ½" outlet positive displacement pump. The pumps are fed from one of the leachate reservoirs. Therefore, each positive displacement pump pulls leachate from its own reservoir and is attached to a manifold line in which each reactor is connected. In a preferred embodiment, a third pump is capable of pumping from either reservoir. Each central and top port is connected to a manifold that leads back to a leachate reservoir. The remaining port on the bottom side of the reactor is for draining one reactor and filling another with its leachate. The selection of the reactor(s), which will receive flow, is determined by manually turning PVC valves on each of the port lines.

Initial Start-Up

In accordance with the subject invention, organic high solid wastes are collected and shredded and compacted. Once compacted, liquid is added in preparation for improved HSLAD operation of the invention. In one embodiment, compaction of shredded solid wastes is performed using a tamper (i.e., plastic or metal tamper). The liquid that is added can include water (i.e., de-chlorinated water) and/or leachate.

The compacted foodstock were loaded onto the HSLAD bioreactors of the invention at very high rates (about 25 times the loading rate of a lab scale reactor system having a total working volume of 5.9L). In one embodiment, the bioreactor(s) of the invention were loaded with a blend of rice, straw, dog food, and paper. During each loading, 4,795 g of paper, 5,611 g of rice straw, and 922 g of dog food were weighed out into empty bins and then loaded onto an improved HSLAD bioreactor of the invention. Three runs (Runs A, B, and C) were performed on the HSLAD bioreactor of Example 1, the results of which are illustrated below in Table 2.

TABLE 2

Exemplary results from prototype reactor runs A, B, and C

| | Units | Run A | Run B | Run C |
|---|---|---|---|---|
| INPUT SOLIDS | | | | |
| Type | | Rice, Paper, Dog food | Rice, Paper, Dog food | Rice, Paper, Dog food |
| Initial feedstock weight | G | 5611, 4000, 741 | 5611, 4000, 741 | 5611, 4000, 741 |
| Total weight | G | 10352 | 11327 | 11398 |
| TS | G | 9648 | 10557 | 10623 |
| Reactor volume | L | 187 | 187 | 187 |
| OUTPUT SOLIDS | | | | |
| Wet weight | G | 28122 | 18824 | 15875 |
| TS | % | 19.4 | 14.5 | 12.4 |
| VS | % VS | 77.2 | 92.0 | 83.0 |
| CONVERSION DATA | | | | |
| Methane yield | dry L@STP/ g VS | 0.06 (0.12)* | 0.091 (0.14)* | 0.10 (0.18)* |
| Final biogas Methane | % CH4 | 58.2 | 56.7 | 60.6 |
| Maximum CH4 production rate | L CH4/L reactors/d | 0.35 (0.44)* | 0.70 | 0.92 |
| Maximum VOA in leachate | mg/L | 20124 | 12649 | 10172 |
| Final VOA in leachate | mg/L | 175 | 277 | 1324 |
| Minimum pH | PH units | 6.91 | 6.58 | 6.75 |
| Final pH | PH units | 7.64 | 7.24 | 7.84 |
| Temperature | ° C. | 35 | 35 | 35 |

*Calculation performed using estimation of volume of gas produced due to leakage losses Comparison of the operational results from Runs B and C using an improved HSLAD system of the invention against a conventional SEBAC system demonstrates that the improved HSLAD system of the invention operates more efficiently than the conventional SEBAC system (see Table 3 below).

TABLE 3

Comparison of first order rate constants from flooded operation of prototype reactor compared to original SEBAC operation.

| | Typical | Flooded Prototype HSLAD Runs | |
|---|---|---|---|
| | SEBAC Run | Run B | Run C |
| Loading rate g VS/L/d | 3.12 | 3.26 | 3.28 |
| Temperature ° C. | 55 | 35 | 35 |
| Feedstock | Sumter Co. MSW | Rice straw, paper, dogfood blend | Rice straw, paper, dogfood blend |
| First order rate constant k d$^{-1}$ | 0.07 | 0.14 | 0.15 |
| Std. error for k | 0.002 | 0.004 | 0.003 |

Figure 5A:
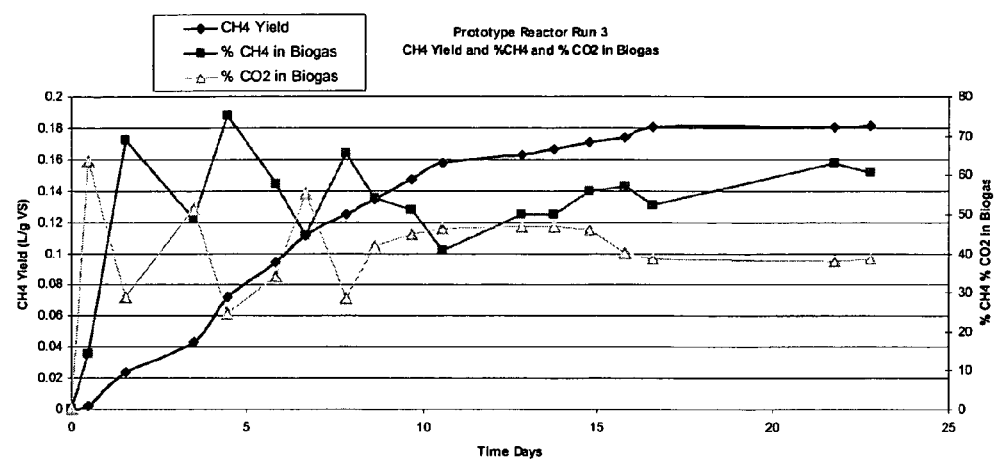
FIGS. 5A–5B are graphical representations of performance data for a bioreactor of the subject invention.
Figure 5B:
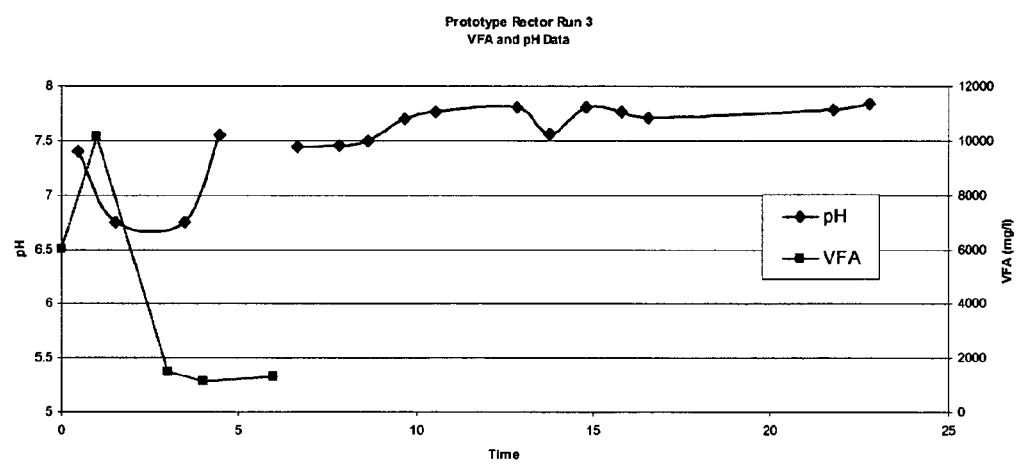

Further, the temporal progression of biogas quality and methane yield is shown in FIG. 5A while the total organic acid levels and pH is shown in FIG. 5B. The rapid speed at which the organic acids are reduced from very high levels >10,000 mg/L during the first several days is a testament to the rapid conversion kinetics of the improved HSLAD systems and processes of the invention.

EXAMPLE 2

Improved HSLAD Start-Up Operation

During the initial loading process of the anaerobic reactor system, liquid (i.e., de-chlorinated water) was added to fill to the top screen 9 of the bottom lid 5 of a bioreactor. The feedstock (rice straw, paper, and dog food) was added to the vessel intermittently along with additional liquid. In one embodiment, 15 gallons of digested dairy manure, 10 gallons of horse manure compost previously run through a conventional, non-flooded SEBAC system to act as a buffering system to the process, and 15 gallons of additional de-chlorinated water is added to fill the reactor to just below the leachate recycle outlet located at the top of the bioreactor.

In another embodiment, the feedstock was compacted using a wooden 2"×4" tamper three times during the filling process. The final compaction observed was 19" below the vessel top, to a calculated density of 129 kg/m$^3$. A leachate reservoir can be supplemented with additional leachate from a conventional SEBAC system (i.e., 5 gallons of SEBAC leachate) and/or with other liquids (i.e., 5 gallons of dechlorinated water). Pump rate was controlled by a Dayton DC speed controller attached to each of the Moyno pumps and efforts were made to keep the flow rate of leachate between 2 and 3 LPM.

In a related embodiment, the pH of the leachate was monitored and an attempt to keep it above 6.5 was made by the addition of NaHCO$_3$, conventional SEBAC leachate, and dechlorinated water. In a preferred embodiment, 2,500 g of NaHCO$_3$ was added into the leachate reservoir for entry into the vessel on days one and two of the improved HSLAD process of the invention. In a related embodiment, the leachate reservoir was emptied and its volume was replaced with dechlorinated water and SEBAC leachate (i.e., on days 1, 2, 3, 4, and 6 of the improved HSLAD process of the invention).

Normal Start-up and Operation

After start-up of a first bioreactor, the remaining reactors are capable of start-up without additional inoculum/leachate or NaHCO$_3$. According to the subject invention, in using a such a system (where the remaining reactors are capable of start-up without additional inoculum/leachate or NaHCO$_3$), when a new reactor is ready to be filled, the vessel is first leak tested by pumping water through the system at elevated speeds for observed gas or liquid leaks. Filling the reactor involves the addition of high solids organic wastes (i.e., 4,790 g of paper, 5,610 g of rice straw, and 922 g of dog food). The remaining of the reactor is then filled with a liquid (i.e., dechlorinated tap water). The new reactor will share its leachate reservoir with the mature reactor to ensure mixing of leachate between the new and mature reactors. This allows for the volatile fatty acids produced by the new reactor to be reduced by the mature reactor and the quick inoculation of the new reactor by providing viable methanogens from the mature reactor.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. An apparatus for sequential batch anaerobic digestion of organic high solids waste comprising:
    a plurality of bioreactors that are flooded with a liquid so as to have no observable headspace;
    a means for storing displaced liquid from the bioreactors;
    a means for transferring liquid between bioreactors and between said storing means and the bioreactors;
    a means for reversing liquid flow between bioreactors; and
    at least one hydraulic pressure sensor.

2. The apparatus of claim 1, wherein the transferring means is a manifold of PVC pipes tapped into the bioreactors.

3. The apparatus of claim 1, wherein the means for accumulating and storing displaced liquid is a vessel external from the bioreactors.

4. The apparatus of claim 3, wherein at least one external vessel is connected to the top, middle, or bottom of at least one bioreactor with a transferring means.

5. The apparatus of claim 3, further comprising a means for heating the external vessel to temperatures of 35° C. or higher.

6. The apparatus of claim 5, wherein the heating means is selected from the group consisting of electrical energy, steam energy, and gas energy.

7. The apparatus of claim 3, wherein the external vessel is $\frac{1}{6}$, $\frac{1}{5}$, $\frac{1}{4}$, $\frac{1}{3}$, $\frac{1}{2}$ or $\frac{1}{1}$ the size of one of the plurality of bioreactors.

8. The apparatus of claim 1, further comprising a means for separating gases from liquids.

9. The apparatus of claim 1, wherein the means for reversing liquid flow between reactors comprises positive displacement pumps.

10. The apparatus of claim 9, wherein the positive displacement pumps are selected from the group consisting of: bellows; double-diaphragm; flexible impeller; gear; oscillating; piston; progressing cavity; rotary lobe; rotary vane; and peristaltic pumps.

11. The apparatus of claim 1, further comprising a screening means suspended within each bioreactor.

12. The apparatus of claim 1, wherein at least one bioreactor is suspended from the ground or located within or beneath the ground.

13. The apparatus of claim 1, wherein the hydraulic pressure sensor is a thermo-coupler.

14. The apparatus of claim 1, wherein the liquid is a combination of de-chlorinated water and leachate.

15. The apparatus of claim 1, wherein the bioreactors have a smaller reactor volume ratio as compared to bioreactors of conventional SEBAC systems.

16. A method for performing high solids anaerobic digestion comprising:
    (a) adding organic high solids waste to a first reactor of a plurality of bioreactors;
    (b) adding a liquid to the first reactor until no headspace is observed in the first bioreactor;
    (c) circulating the liquid from the first bioreactor to other bioreactors;
    (d) monitoring hydraulic pressure in at least one bioreactor and, if there is a change in hydraulic pressure, reversing the flow of circulated liquid;
    (e) continuing anaerobic digestion of the waste to substantial completion to produce gas via continuous recirculation of the liquid to other bioreactors.

17. The method of claim 16, further comprising the steps of collecting and coarsely shredding the organic high solid waste and compacting the shredded organic high solid waste prior to adding the liquid.

18. The method of claim 16, further comprising the step of removing liquid displaced from a bioreactor to an external vessel.

19. The method of claim 16, further comprising the step of separating methane gas from the liquid.

20. The method of claim 19, wherein the separation process is accomplished by employing gravity or centrifugal force to the liquid in the external vessel.

21. The method of claim 16, wherein the liquid is a mixture of de-chlorinated water and leachate.

* * * * *

UNITED STATES PATENT AND TRADEMARK OFFICE
CERTIFICATE OF CORRECTION

| | | |
|---|---|---|
| PATENT NO. | : 7,153,428 B2 | Page 1 of 1 |
| APPLICATION NO. | : 11/117269 | |
| DATED | : December 26, 2006 | |
| INVENTOR(S) | : David P. Chynoweth et al. | |

It is certified that error appears in the above-identified patent and that said Letters Patent is hereby corrected as shown below:

Column 7,
Lines 57-58, "The from a leachate reservoir" should read --The flow of leachate to a bioreactor from a leachate reservoir--.

Signed and Sealed this

First Day of May, 2007

JON W. DUDAS
*Director of the United States Patent and Trademark Office*